United States Patent [19]

Garzia

[11] Patent Number: 4,474,801
[45] Date of Patent: Oct. 2, 1984

[54] α-AMINO-γ-BUTYROLACTONES FOR TREATING ALCOHOL DEPENDENCE

[75] Inventor: Aldo Garzia, Milan, Italy

[73] Assignee: Istituto Chemioterapico Italiano, SpA, Milan, Italy

[21] Appl. No.: 441,294

[22] Filed: Nov. 12, 1982

[51] Int. Cl.$^3$ ............................................ A61K 31/335
[52] U.S. Cl. .................................................... 424/279
[58] Field of Search .......................................... 424/279

[56] References Cited

U.S. PATENT DOCUMENTS 3,061,614 10/1962 Sweeney ......................... 260/343.6
3,133,138 12/1963 Franko ............................. 260/343.6
3,952,020 4/1976 Stapp ................................ 260/343.6
3,968,233 7/1976 Garzia .............................. 260/343.6

Primary Examiner—Stanley J. Friedman
Attorney, Agent, or Firm—Bernard, Rothwell & Brown

[57] ABSTRACT

Compounds corresponding to the formula:

$$H_2C\text{------}CH\text{--}NH\text{--}\underset{\underset{O}{\|}}{C}\text{--}OR$$
$$H_2C\text{------}\underset{\underset{O}{\diagdown\diagup}}{C}=O$$

where R is an alkyl group of 3 to 5 carbon atoms, are useful in treating alcohol dependence.

6 Claims, No Drawings

α-AMINO-γ-BUTYROLACTONES FOR TREATING ALCOHOL DEPENDENCE

FIELD OF THE INVENTION

This invention relates to certain alkyl carbamate derivatives of α-amino-γ-butyrolactone, and in particular to the use of certain alkyl carbamate derivatives of α-amino-γ-butyrolactones in the treatment of alcohol dependence.

BACKGROUND OF THE INVENTION

The treatment of alcohol dependence is of considerable importance to those afflicted with the problem, to the medical profession and to society in general, but safe and effective treatments for the condition are still needed and sought after. When an alcohol-dependent person stops ingesting alcohol or alcoholic beverages, complete detoxification is probably not achieved in a few days of "sobering up". It is thought that several months of abstinence from alcohol are required before vital organ systems are restored to normal. During this postwithdrawal phase, drug therapy is often considered beneficial in discouraging a patient from resuming the use of alcohol but the drug therapy presently used to treat alcohol-dependent people is attended by numerous drawbacks.

The most common drug used in this postwithdrawal treatment is disulfiram. Disulfiram apparently acts as a chelating agent capable of chelating the zinc of alcohol dehydrogenase, the iron and molybdenum of aldehyde dehydrogenase and the copper of dopamine-beta-hydroxylase. Whatever the precise mechanism by which disulfiram operates, patients receiving the drug refrain from drinking alcoholic beverages to avoid unpleasant and possibly toxic or even fatal effects stemming from the interaction of disulfiram with ethanol. Within a few minutes after ingesting even minute quantities of alcohol in disulfiram-treated patients, a remarkable reaction often occurs. The patient first notes a feeling of warmth in the face. The skin, especially in the upper chest and face, becomes bright red and a pounding sensation occurs in the head and chest. In addition, respiratory difficulties, nausea, vomiting, sweating, weakness, dizziness, blurred vision, and confusion may also be part of the reaction. It is unclear exactly how long after a single dose of disulfiram a reaction will still occur, although 12 to 24 hours is a common estimate. With large doses of alcohol and disulfiram, the reaction can be extremely severe and life threatening. The reaction is usually proportional to the amount of alcohol ingested and the dose of disulfiram. Reactions may last a few minutes in mild cases to several hours in severe ones. Some patients taking disulfiram accidentally ingest ethanol or deliberately take it in an attempt to verify the efficacy of the drug or to kill themselves. Some patients with brief mild reactions never seek medical attention; some prolonged severe reactions require immediate medical attention.

In addition to these hazardous reactions, disulfiram's effectiveness is relatively short-lived. For instance, a single dose of disulfiram may only be effective for about 12 to 24 hours. This limits the drug's clinical usefulness because disulfiram-treated patients can easily discontinue use on their own, making it difficult to monitor and maintain adherence to prescribed disulfiram treatment. Applicant has overcome these drawbacks with the present invention which provides a method of treating alcohol dependence without the hazardous reactions that result from combining disulfiram with alcohol, particularly ethanol, and which is effective for a longer period of time.

OBJECTS OF THE INVENTION

It is an object of this invention to provide a method for treating alcohol dependence which does not produce hazardous side effects and is effective for a substantial period of time after administration.

SUMMARY OF THE INVENTION

Applicant's invention provides a method for treating warmblooded mammals, including humans, for alcohol dependence by administering an effective amount of an alkyl carbamate derivative of α-amino-γ-butyrolactone to inhibit a patient from ingesting alcohol or alcoholic beverages.

DETAILED DESCRIPTION OF THE INVENTION

In the method of applicant's invention, an alcohol-dependent patient is treated by the administration of effective quantities of certain alkyl carbamate derivatives of α-amino-γ-butyrolactone represented by the following formula:

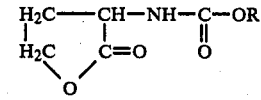

wherein R is an alkyl group of 3 to 5 carbon atoms. Applicant has discovered that these compounds, particularly α-n-butoxycarbonyl-amino-γ-butyrolactone (hereinafter alternatively referred to as AP-28), are useful in the treatment of alcohol-dependent warmblooded mammals, including humans. It has been found, however, that D-isomeric form of AP-28 is not active for the purpose of treating alcohol dependence, while the L-isomeric form of AP-28 is active and effective for that purpose. All further references to AP-28 and the compounds described by the above formula, therefore exclude the above identified isomer which as been found to be ineffective in the treatment of alcohol dependence.

The identified compounds, and especially AP-28 can be conveniently administered orally or intraperitoneally, depending on the needs of the subject treated. In some extreme cases, doses higher than 2000 mg/kg may be indicated. AP-28 is generally more effective when administered intraperitoneally than orally and, therefore, smaller doses can be administered intraperitoneally to achieve a given effect. However, oral administration is more convenient and more acceptable to human patients and therefore is often the preferred mode for treating humans.

Generally, the preferred dose of AP-28 for humans is about 1 gram per day, preferably in two administrations each day. After 3 days of treatment with AP-28 in this manner, the desire for alcohol is suppressed up to about 30 days. The selection of the proper dosage and dose form is well within the ability of one of ordinary skill in the art and it is not intended that the invention be limited thereby.

The compounds of the present invention are generally prepared by reacting the corresponding alkyl chloroformate with α-amino-γ-butyrolactone at reduced temperatures and in the presence of pyridine. α-amino-γ-butyrolactone is a known compound available commercially. It can be prepared, for example, by the method of J. E. Livak et al., J. Am. Chem. Soc. 67, p. 2218 (1945). Generally the process of preparing compounds of the present invention includes the steps of mixing α-amino-γ-butyrolactone hydrobromide, one mole, with more than about 2 moles of pyridine in the presence of water as solvent, cooling to about 0°±5° C. adding about 1 to 1.25 moles of alkyl-chloroformate, allowing to stand at about 0° for a period of time sufficient for the reaction to go substantially to completion, warming to room temperature and recovering the product therefrom. Recovery of the product is easily accomplished by reducing the volume of the reaction mixture, e.g., by evaporation, and chilling in an ice bath to crystallize the product.

The effectiveness and utility of the compounds and applicant's method in treating alcohol dependence in warmblooded mammals is further illustrated by the following examples:

EXAMPLE I

Wistar rats were selected to test the effectiveness of applicant's method in the suppression of alcohol intake. Following administration of an anesthetic dose of 4.5 g/kg of ethanol (25% solution) intraperitoneally, rats were tested for their sensitivity to the soporific effect of ethanol. Recordings were made of the onset and duration of sleep-time, indicated by the disappearance and return of the righting reflex. Animals with the shortest sleep-time were caged individually and maintained on a 12 hour light-dark cycle. The same procedures were carried out in rats with the longest sleep-time. Ethanol solution (15%) and water were given in graduated bottles. The position of the bottles was changed irregularly to prevent the development of a position habit and ensure that the rats initially sampled both available fluids. Fluid intake was recorded at the same time each day. Only the animals with the shortest sleep-time started to drink ethanol solution. In fact, in these animals, the absolute ethanol intake after two weeks was 4.3±0.85 g/kg/day, while in those with the longest sleep-time it was 0.75±0.13 g/kg/day. After one month of alcohol exposure and baseline alcohol intake recordings, animals with the shortest sleep-time were randomly divided into two groups. For the following 3 days, one group was injected with α-n-butoxycarbonyl-amino-γ-butyrolactone (200 mg/kg, i.p.), combined with a pharmaceutically acceptable carrier, twice daily for three successive days, while the control group received injections of saline. Monitoring of fluid intake and body weight was continued for a further 5 days following termination of the injection period.

Table I shows the mean ethanol consumption, expressed in terms of absolute ethanol quantity, prior to, during and after α-n-butoxycarbonyl-amino-γ-butyrolactone injection. While rats in the control group showed no significant difference in ethanol consumption, the group treated with α-n-butoxycarbonyl-amino-γ-butyrolactone, referred to as the test group, showed a complete suppression of ethanol intake. Ethanol consumption remained reduced during the 5-day post-injection period. Concomitant with the suppression of voluntary ethanol intake, there was no significant reduction in total fluid intake or body weight produced by the treatment.

The data in Example I shows that the rats drank a significant percentage of their daily fluid intake as 15% ethanol solution, corresponding to about 4–5 g. ethanol/kg/day. The injection of α-n-butoxycarbonyl-amino-γ-butyrolactone intraperitoneally at the dose of 200 mg/kg, twice daily for 3 consecutive days, decreased ethanol intake by about 80% on the days of treatment, but did not reduce total fluid intake. Ethanol intake remained significantly reduced up to the 5th day following cessation of administration. It was found that up to a concentration of $10^{-3}$ M, α-n-butoxycarbonyl-amino-γ-butyrolactone inhibits neither alcohol-dehydrogenase nor aldehyde-dehydrogenase in rat liver homogenates, nor dopamine-β-hydroxylase in homogenates of adrenal medulla or hypothalamus of rats.

EXAMPLE II

Twelve alcohol-dependent human patients were administered 2 grams of α-n-butoxycarbonyl-amino-γ-butyrolactone (AP-28) daily for 2 days. The dosage was administered in tablets containing 0.5 grams each of AP-28 four times a day. At the end of the treatment all of the patients indicated that they had little or no desire at all to drink alcoholic beverages. When the patients ingested alcoholic beverages after treatment, none of the potentially hazardous reactions encountered when both disulfiram and alcoholic beverages are ingested by a patient were experienced. In addition, the patients indicated little or no desire to resume alcohol consumption for a period of about 30 days after treatment with AP-28.

What is claimed is:

1. A method for treating a warmblooded mammal for alcohol dependence, wherein said mammal is an alcoholic requiring such treatment, comprising administering to said warmblooded mammal an effective amount of a compound represented by the formula

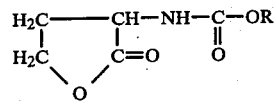

wherein R is an alkyl of 3–5 carbon atoms except that R does not include the D-isomeric form of α-n-butoxycarbonyl-amino-γ-butyrolactone.

2. A method as recited in claim 1 wherein said compound is administered orally.

3. A method as recited in claim 1 wherein said compound is administered intraperitoneally.

4. A method as recited in claims 1, 2 or 3 wherein said compound is the L-isomeric form of α-n-butoxycarbonyl-amino-γ-butyrolactone, and said compound is administered to a human.

5. A method for treating a human for alcohol dependence, wherein said human is an alcoholic requiring such treatment, as recited in claim 4 wherein said compound is administered in tablet form 4 times a day in an amount sufficient to suppress said patient's desire for alcohol.

6. A method for treating a human for alcohol dependence, wherein said human is an alcoholic requiring such treatment, as recited in claim 4 wherein 1 gram of said compound is administered daily for a period of about three days.

* * * * *